United States Patent
Massmann et al.

(10) Patent No.: US 6,605,568 B1
(45) Date of Patent: Aug. 12, 2003

(54) PROCESS FOR MAKING A DOWNSTREAM PROCESSABLE AMMONIUM GLYPHOSATE PASTE

(75) Inventors: Brent D. Massmann, Ballwin, MO (US); Richard M. Kramer, Chesterfield, MO (US); John T. Wang, St. Louis, MO (US); Marc Emile Toussaint, deceased, late of Corroy-le-Grand (BE), by Andree-Marie Toussaint, legal representative

(73) Assignees: Monsanto Technology LLC, St. Louis, MO (US); Monsanto Europe, S.A., Brussels (BE)

( * ) Notice: Subject to any disclaimer, the term of this patent is extended or adjusted under 35 U.S.C. 154(b) by 0 days.

(21) Appl. No.: 09/627,078

(22) Filed: Jul. 27, 2000

Related U.S. Application Data
(60) Provisional application No. 60/146,243, filed on Jul. 28, 1999.

(51) Int. Cl.[7] .............................. A01N 57/02; C07F 9/38
(52) U.S. Cl. ...................... 504/127; 504/128; 504/206; 562/17
(58) Field of Search ................................. 504/206, 127, 504/128; 562/17

(56) References Cited

U.S. PATENT DOCUMENTS

| | | |
|---|---|---|
| 3,671,612 A | 6/1972 | Roszinski et al. |
| 4,405,531 A | 9/1983 | Franz |
| 4,840,659 A | 6/1989 | Franz |

(List continued on next page.)

FOREIGN PATENT DOCUMENTS

| | | | |
|---|---|---|---|
| EP | 0 394 211 A1 | 10/1990 | |
| EP | 0 582 561 | 2/1994 | .......... A01N/57/20 |
| FR | 2 692 439 A1 | 12/1993 | |

(List continued on next page.)

OTHER PUBLICATIONS

International Search Report for Application No. PCT/US00/20337, dated Nov. 15, 2000, 2 pgs.
Takahashi, Gunji, "*Studies on the Pesticide Formulation and Jet Mill*", Funtai to Kogyo, 1987, pp. 35–40, vol. 19(10)—as abstracted by CAPLUS CA:109:2308.
"*The Merck Index*", 13th Ed., 2001, p. 87, Merck Research Laboratories Div. of Merck & Co., Inc., Whitehouse Station, NJ.

*Primary Examiner*—S. Mark Clardy
(74) *Attorney, Agent, or Firm*—Senniger, Powers, Leavitt & Roedel; Joseph A. Schaper

(57) ABSTRACT

A process is provided for preparing a downstream processable ammonium glyphosate paste, comprising mixing in a suitable vessel (i) particulate glyphosate acid, (ii) ammonia in an amount of about 0.8 to about 1.25 moles per mole of the glyphosate acid, and (iii) water in an amount of about 10% to about 25% by weight of all materials being mixed in the vessel, thereby causing a reaction of the glyphosate acid and ammonia that generates heat causing partial evaporation of the water, and forms an ammonium glyphosate paste having a moisture content of about 5% to about 20% by weight.

A process is also provided for preparing a dry granular herbicidal composition, comprising (a) forming an ammonium glyphosate paste as described above and thereafter, if the moisture content of the paste is greater than about 15% by weight, applying heat and/or vacuum to reduce the moisture content to about 5% to about 15% by weight; (b) thereafter adding to the paste, with mixing, one or more surfactants in a weight ratio of total surfactant to ammonium glyphosate of about 1:9 to about 1:3 to form an extrudable wet mix; (c) extruding the wet mix to form extrudate strands that break to form moist coherent granules; and (d) drying the granules to produce the dry granular composition.

44 Claims, 4 Drawing Sheets

U.S. PATENT DOCUMENTS

| | | | |
|---|---|---|---|
| 5,047,079 A | 9/1991 | Djafar et al. ................... 71/86 |
| 5,070,197 A | 12/1991 | Chin et al. ..................... 544/11 |
| 5,266,553 A | 11/1993 | Champion .................. 504/206 |
| 5,324,708 A | 6/1994 | Moreno ....................... 504/206 |
| 5,410,075 A | 4/1995 | Moreno ........................ 562/17 |
| 5,430,005 A | 7/1995 | Kassebaum et al. |
| 5,612,285 A | 3/1997 | Arnold ....................... 504/206 |
| 5,614,468 A | 3/1997 | Kramer et al. ............... 504/206 |
| 5,633,397 A | 5/1997 | Gillespie et al. ............... 562/17 |
| 5,656,572 A | 8/1997 | Kuchikata et al. |
| 5,693,593 A | 12/1997 | Arnold ....................... 504/206 |
| 5,716,903 A | 2/1998 | Kramer et al. .............. 504/206 |
| 6,448,434 B1 | 9/2002 | Kramer |

FOREIGN PATENT DOCUMENTS

| | | | |
|---|---|---|---|
| JP | 59-109502 | 6/1984 | |
| JP | 59-139391 | 8/1984 | |
| JP | 01-215805 | 8/1989 | |
| JP | 02-032037 | 2/1990 | |
| JP | 06-256121 | 9/1994 | |
| WO | WO87/04595 | 8/1987 | .......... A01N/57/20 |
| WO | WO90/07275 | 7/1990 | .......... A01N/57/20 |
| WO | WO92/12637 | 8/1992 | .......... A01N/57/20 |
| WO | WO 92/18513 A1 | 10/1992 | |
| WO | WO94/10844 | 5/1994 | .......... A01N/57/20 |
| WO | WO 96/40696 A1 | 12/1996 | |
| WO | WO 96/40697 A1 | 12/1996 | |

PROCESS FOR MAKING A DOWNSTREAM PROCESSABLE AMMONIUM GLYPHOSATE PASTE

This application claims the benefit of U.S. Provisional Application No. 60/146,243 filed Jul. 28, 1999.

FIELD OF THE INVENTION

The present invention relates to preparation of a herbicidal formation useful in agriculture and in other situations where control of weeds or other vegetation is desired. In particular, it relates to a process for preparing a herbicidal paste containing as an active ingredient N-phosphonomethylglycine (glyphosate) in the form of the ammonium salt thereof, the paste being suitable for downstream processing to prepare a dry water-soluble granular herbicidal composition further containing a surfactant.

BACKGROUND OF THE INVENTION

Glyphosate herbicides, especially herbicides comprising a water-soluble salt of glyphosate, are well known. Specifically, the monoammonium salt of glyphosate is disclosed as a useful herbicide for example in U.S. Pat. No. 4,405,531 to Franz. Unless the context demands otherwise, "ammonium glyphosate" herein refers to the monoammonium salt of glyphosate, which has the chemical formula

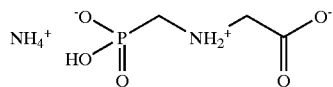

it being understood that the mole ratio of ammonium cations to glyphosate anions in such a salt is not necessarily exactly 1. A slight molar excess of either ammonium cations or glyphosate anions, for example providing a mole ratio of about 0.8 to about 1.25, is not inconsistent with the term "ammonium glyphosate" as used herein.

Ammonium glyphosate is the primary salt of choice in the preparation of dry glyphosate herbicide formulations. A "dry" formulation herein is a composition that is solid, usually particulate, wherein particles are either aggregated as in a granular composition or non-aggregated as in a powder. The word "dry" in this context does not imply that the formulation is necessarily free of water or other liquid, only that it is dry to the touch. Dry formulations can contain up to about 5% by weight of water, but more typically the water content is less than about 1%, for example about 0.5% or lower.

Dry formulations of glyphosate herbicides, like the corresponding liquid (normally aqueous) formulations, typically contain one or more surfactants in addition to the glyphosate salt. Surfactants are important components of glyphosate formulations because, when a glyphosate formulation is diluted, dissolved or dispersed in water for application by spraying to foliage of plants, the surfactants assist in retention of droplets of the spray by the foliage, adhesion of the spray droplets to the foliar surface and penetration of the glyphosate through the hydrophobic cuticle that covers the foliar surface, by these means and possibly in other ways enhancing herbicidal effectiveness of the glyphosate spray. Specific surfactant types differ greatly in the degree to which they enhance herbicidal effectiveness of glyphosate, and it is therefore important to select a suitable surfactant or combination of surfactants, as demonstrated by Wyrill & Burnside, *Weed Science* 25, 275–287, 1977.

The optimum amount of surfactants for delivering the desired herbicidal effectiveness is typically in the range of about 0.2 to about 1 part by weight of surfactant per part by weight of glyphosate, expressed as acid equivalent (a.e.) When it is desired to formulate the glyphosate herbicide in dry form, it can be difficult to load such an amount of surfactant into the formulation without the formulation becoming sticky, having a tendency to cake or lacking good pouring or flow properties.

Three approaches are known in the art to overcoming the problems of providing a sufficient amount of surfactant in a dry glyphosate formulation. The first and most straightforward is to add an inert particulate carrier that can absorb or adsorb the surfactant to a sufficient degree to avoid the problems mentioned above. The carrier can be insoluble but dispersible in water, as in the case for example of particulate silica, or it can be soluble in water, as in the case for example of ammonium sulfate. However, the addition of such a carrier inevitably reduces the maximum loading of glyphosate herbicide that can be accommodated in the formulation and for this reason adds substantially to the cost per unit of glyphosate a.e. of the resulting formulation. In this regard it should be recognized that the cost of processing is a significant element in the cost of a dry formulation, and the cost of processing is dictated by the volume of product produced. A product that has to be produced in high volume because its loading of active ingredient is low therefore suffers a significant penalty in cost per unit of active ingredient.

A second approach, as illustrated by U.S. Pat. No. 4,931,080 to Chan & Djafar, is to select a surfactant that is solid at ambient temperature. In this approach the surfactant is melted before mixing with particulate glyphosate herbicide and water, so that upon drying and cooling the surfactant solidifies to form a matrix surrounding the herbicide particles. There is no need for an inert carrier. Unfortunately the list of surfactants that are solid at ambient temperature excludes many surfactants that are among the most effective in potentiating glyphosate herbicidal activity.

A third approach, therefore, as illustrated by U.S. Pat. No. 5,656,572 to Kuchikata et al. (the '572 patent), is to select a surfactant that is liquid at ambient temperature and to ensure that the glyphosate herbicide particles themselves absorb or adsorb a sufficient amount of surfactant to avoid the problems of stickiness, caking and poor flowability. The '572 patent teaches that this can be achieved most readily if the surfactant selected is one that gels when added to water. However, it is also clear that the absorption and/or adsorption properties of the glyphosate herbicide particles greatly influence the amount of a liquid surfactant that can be included in a formulation.

Ammonium glyphosate is the preferred salt for use in preparing dry glyphosate formulations for a number of reasons, but perhaps mainly for the reason that ammonium glyphosate is relatively non-hygroscopic. Salts favored for preparation of aqueous formulations, such as the isopropylammonium salt or the trimethylsulfonium salt, are very difficult to dry down to a crystalline state and, once dry, have a strong tendency to reabsorb water. The sodium salt, disclosed to be useful in dry glyphosate herbicide formulations for example in International Patent Application No. WO 87/04595, is much less hygroscopic than these salts but nonetheless requires packaging with a very water-impermeable material to avoid absorption of water vapor from the atmosphere and consequent loss of free-flowing properties. U.S. Pat. No. 5,324,708 to Moreno et al. discloses a process for preparing a non-hygroscopic monoammonium glyphosate; however, dry ammonium glyphosate prepared by any known process is adequately non-hygroscopic for most practical purposes.

Commercial herbicides in the form of dry water-soluble granules containing ammonium glyphosate together with a liquid surfactant include Roundup® Dry, Roundup® Max and Rival® herbicides, marketed by Monsanto Company in several countries.

Numerous granulation processes have been disclosed that are suitable for preparing water-soluble or water-dispersible granules of ammonium glyphosate with a liquid surfactant. One such process is pan granulation. However, a more widely used granulation process for a dry ammonium glyphosate formulation is extrusion granulation. An example of such a process is one that is broadly as described in British Patent No. 1 433 882 ("the '882 patent"), except that the primary active ingredient, namely ammonium glyphosate, is water-soluble rather than water-insoluble as in the process of the '882 patent. In this process, ammonium glyphosate is mixed with surfactant and a small amount of water to form an extrudable wet mix, which is then extruded to form strands of extrudate that break spontaneously at the point of extrusion or shortly thereafter to form short cylindrical granules, which are then dried. Drying is preferably conducted in a fluid-bed dryer. The amount of water in the wet mix is critical to the operation. If the mix is too wet, the strands of extrudate do not readily break to form discrete granules. If the mix is too dry, the resulting granules are friable and tend to generate a significant amount of fine particulate material during drying or later, during handling of packaged granules. Optionally a rolling or tumbing step can be inserted between extruding and drying, as taught in U.S. Pat. No. 5,443,764 to Lloyd, to improve uniformity of granule size and shape.

U.S. Pat. No. 5,070,197 to Chin et al. discloses a continuous process in which a Bronsted acid, for example glyphosate acid, is intimately mixed in an extruder with a Bronsted base, for example ammonia, essentially without addition of "extraneous solvent" such as water, although it is stated that a small amount of water (usually about 4% by weight) is optionally added upstream for "initial lubricity". An acid-base reaction is said to occur in the extruder, forming a salt which is extruded to form a dry composition.

U.S. Pat. No. 5,266,553 to Champion & Harwell discloses a process for preparing a dry water-soluble of a herbicide having a carboxylic acid functionality, wherein a solution of slurry of the salt is prepared by reacting the herbicide in acid form with a sufficient amount of a neutralizing base in the presence of water to neutralize the herbicide by about 98 to about 100 mole percent, and the solution or slurry is then dried. The process is primarily directed to ammonium and alkylammonium salts of substituted benzoic acid and phenoxy-substituted carboxylic acid herbicides, but the process is said to be useful also for salts of glyphosate.

The process by which ammonium glyphosate, used as an intermediate in making a finished formulation, is prepared has been found to affect to a great degree the absorptive and/or adsorptive properties of particles of the ammonium glyphosate with respect to a liquid surfactant. The absorbency and adsorbency properties of the ammonium glyphosate particles are especially important where, as is desirably the case, an extrusion process such as that disclosed in the above-referenced '882 patent is to be used in preparing the finished formulation.

Solid-state reaction of glyphosate acid and ammonium bicarbonate, as disclosed for example in the above-referenced '572 patent, tends to produce a particulate ammonium glyphosate having sufficient absorbency and/or adsorbency to permit satisfactory formulation with up to about 25% by weight of a liquid surfactant such as polyoxyethylene tallowamine. By contrast, reaction of a slurry of glyphosate acid with anhydrous ammonia or aqueous ammonia (ammonium hydroxide) followed by drying to form an ammonium glyphosate powder tends to produce relatively non-absorptive or non-adsorptive ammonium glyphosate particles.

Because anhydrous and aqueous ammonia are much lower-cost sources of the ammonium cation than ammonium bicarbonate, numerous efforts have been made to develop processes wherein glyphosate acid is reacted with anhydrous or aqueous ammonia, yet wherein the resulting ammonium glyphosate is suitable for downstream formulation with surfactant, especially a liquid surfactant. To date, success has been achieved only when the reaction occurs in the presence of very small amounts of water, for example about 7 parts or less by weight of water per 100 parts by weight of dry ingredients. U.S. Pat. No. 5,614,468 to Kramer et al. discloses such a process wherein solid particulate glyphosate acid is reacted with aqueous ammonia, and U.S. Pat. No. 5,633,397 to Gillespie et al. discloses such a process wherein solid particulate glyphosate acid is reacted with gaseous anhydrous ammonia.

Unfortunately the solid-state processes mentioned immediately above are more difficult to control than a process wherein glyphosate and ammonia are reacted in an aqueous medium. In addition, the exothermic nature of the reaction gives rise to a need for dissipation of heat, which can present problems in a solid-state medium because of the poor heat transfer coefficient of such a medium, the relative difficulty of ensuring adequate mixing and the limited potential for evaporative cooling where moisture content of the reaction medium is so low.

Thus to date the formulator wishing to prepare a surfactant-containing dry granular ammonium glyphosate formulation, particularly where the base to be reacted with glyphosate acid is anhydrous or aqueous ammonia, has been obliged to use a solid-state reaction system, with all its attendant problems. The alternative, which is to dry the product of a reaction of glyphosate acid and ammonia in an aqueous medium, is unsatisfactory because it generates a form of particulate ammonium glyphosate that does not adequately absorb or adsorb the desired surfactant.

The present invention provides a process wherein glyphosate acid is reacted with anhydrous or aqueous ammonia in a medium that permits superior mixing of the reactants with greater ease of temperature control by comparison with solid-state reaction systems, yet surprisingly generates ammonium glyphosate in a form that is readily suitable for blending with surfactant and extrusion to form dry water-soluble or water-dispersible granules.

SUMMARY OF THE INVENTION

Figure 1:
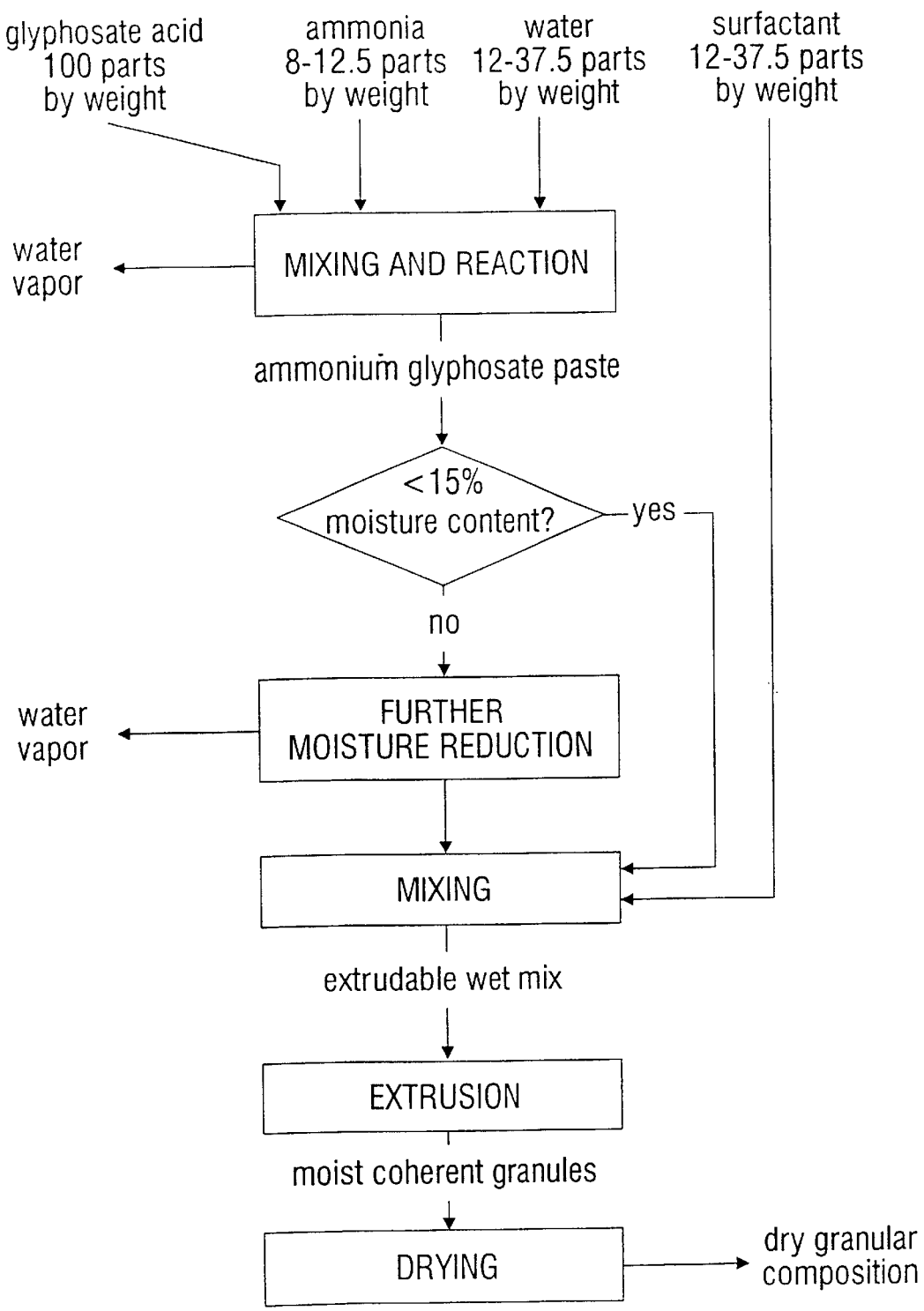
FIG. 1 shows a process flow diagram of a process of the invention for preparing a dry granular herbicidal composition.

A process is provided for preparing a downstream processable ammonium glyphosate paste, comprising mixing in a suitable vessel (i) particulate glyphosate acid, (ii) ammonia in an amount of about 0.8 to about 1.25 moles per mole of the glyphosate acid, and (iii) water in an amount of about 10% to about 25% by weight of all materials being mixed in the vessel, thereby causing a reaction of the glyphosate acid and ammonia that generates heat causing partial evaporation of the water, and forms an ammonium glyphosate paste having a moisture content of about 5% to about 20% by weight.

The term "downstream processable" herein means that the ammonium glyphosate paste is readily capable, upon further reduction in moisture content if necessary to about 5% to about 15% by weight, of being further processed by extrusion granulation with surfactant at a weight ratio of surfactant to ammonium glyphosate of about 1:9 to about 1:3 to form a dry granular herbicidal composition.

A process is also provided for preparing a dry granular herbicidal composition, comprising (a) mixing in a suitable vessel (i) particulate glyphosate acid, (ii) ammonia in an amount of about 0.8 to about 1.25 moles per mole of the glyphosate acid, and (iii) water in an amount of about 10% to about 25% by weight of all materials being mixed in the vessel, thereby causing a reaction of the glyphosate acid and ammonia to generate heat that causes partial evaporation of the water and to form an ammonium glyphosate paste, and thereafter, if the paste has a moisture content greater than about 15% by weight, applying heat and/or vacuum to reduce the moisture content of the paste to about 5% to about 15% by weight; (b) thereafter adding to the paste, with mixing, one or more surfactants in a weight ratio of total surfactant to ammonium glyphosate of about 1:9 to about 1:3 to form an extrudable wet mix; (c) extruding the wet mix to form extrudate strands that break to form moist coherent granules; and (d) drying the granules to produce the dry granular composition. Optionally the process comprises a further step (e) of classifying the dried granules to remove or recycle granules, fragments of granules and aggregates of granules that are outside a desired size range.

In the step of mixing glyphosate acid, ammonia and water in either of the processes described above, all or part of the required water can be present as moisture associated with the glyphosate acid, for example in a wet cake form of the glyphosate acid, and/or as the water component of aqueous ammonia. Water present in a glyphosate acid composition and/or in an ammonia composition added as ingredients in the mixing step is included in the 10% to 25% by weight of water specified above, as is water present in any other ingredient that can optionally be added at this stage.

Where no other ingredients are included, the present processes require, for each 100 parts by weight of glyphosate acid, about 8 to about 12.5 parts by weight of ammonia and about 12 to about 37.5 parts by weight of water (including water supplied as a component of a glyphosate acid composition and/or an ammonia composition). The process described above for preparing a dry granular herbicidal composition additionally requires, for each 100 parts by weight of glyphosate acid, about 12 to about 37.5 parts by weight of surfactant.

In the process for preparing a dry granular herbicidal composition, the extrudable wet mix formed in step (b) is preferably of a consistency such that the extrudate strands formed in step (c) break spontaneously upon extrusion to form the granules. However, optionally step (c) further comprises breaking or cutting the extrudate strands to form the granules. Whether or not step (c) comprises such a breaking or cutting operation, optionally step (c) comprises rolling and/or tumbling the moist granules to impart to the granules a more spherical shape and greater uniformity of size.

In a preferred embodiment, the step of mixing glyphosate acid, ammonia and water is operated in a continuous mode. However, this mixing step can alternatively be operated in a batch mode. In a particularly preferred embodiment, the entire process for preparing a dry granular herbicidal composition is operated in a continuous mode. In another particularly preferred embodiment of the process for preparing a dry granular herbicidal composition, the amount of water present in the mixing step (a) is not greater than about 15% by weight and the heat of reaction is sufficient to reduce the water content of the resulting ammonium glyphosate paste to about 5% to about 10% by weight, so that applying heat to further remove water from the paste is unnecessary.

A major advantage of the present process over previously known processes involving solid-state reaction to provide downstream processable ammonium glyphosate is the much greater speed with which the reaction is completed, requiring a much shorter residence time of glyphosate in the reaction vessel. This short residence time, which can be one-tenth or less of the residence time required by a solid-state process, makes it practicable on a manufacturing scale to operate the process in continuous mode rather than in batch mode.

DETAILED DESCRIPTION OF THE INVENTION

In a process of the invention for preparing an ammonium glyphosate paste, which process is also at least part of the first step, i.e., step (a) as defined above, of a process of the invention for preparing a dry granular herbicidal composition, a paste predominantly comprising ammonium glyphosate is produced by mixing solid particulate glyphosate acid, anhydrous or aqueous ammonia and water in the relative amounts stated, so that an acid-base reaction occurs between the glyphosate acid and the ammonia to form the ammonium glyphosate. This mixing step can take place in any suitable apparatus comprising a vessel equipped with mixing means capable of blending solid and liquid materials to produce a paste. Food mixers, planetary mixers, ribbon blenders and kneaders are illustrative examples. Where anhydrous ammonia is used, it is important that the mixing means should in operation create and maintain a large interfacial area between the paste and the internal atmosphere of the mixing vessel. This interfacial area, herein referred to as the gas-paste interface, is critical to efficient reaction of glyphosate acid with ammonia gas present in the internal atmosphere. Any mixing means that constantly entrains a significant volume of gas in the paste can be suitable.

A particularly suitable mixing means is an assembly comprising a rotatable shaft having one or more screw elements coaxial with the shaft and bearing a plurality of radially disposed pins and/or paddles. Upon rotation of the shaft, the screw elements of such an assembly cause bulk movement of paste in a direction parallel to the shaft, while simultaneously the pins and/or paddles constantly mix the paste and create a large gas-paste interface. More than one of such shafts can be present, disposed parallel to one another and rotatable in the same direction or in opposite directions.

Preferably the mixing and reaction occur in a substantially enclosed chamber having at an input end an aperture suitable for introduction of the particulate glyphosate acid, having at an output end an aperture suitable for discharge of the ammonium glyphosate paste, and having between the input and output ends one or more ports suitable for introduction of ammonia and water. Optionally further ports are present near the output end for exhaust of water vapor and, if necessary, excess ammonia.

In an especially preferred embodiment, the mixing apparatus is a continuous processor comprising such a chamber elongated in a substantially horizontal dimension, wherein are rotatably disposed one or more, most preferably one or two, shafts as described above, each on an axis parallel to the elongated dimension of the chamber. Operation of the apparatus by rotation of the shafts effects (i) feeding of the glyphosate acid into the chamber through the aperture at the input end, (ii) mixing of the ingredients to form a reaction mass having a large gas-paste interface (iii) transport of the reaction mass and the resulting ammonium glyphosate paste towards the output end of the chamber, and (iv) discharge of the ammonium glyphosate paste from the aperture at the output end. Water and ammonia are injected through ports located between the input and output ends. Preferably the water is injected at or near the input end and the ammonia is injected at a sufficient distance from the input end to permit thorough mixing of the glyphosate acid and the water prior to substantial exposure of the glyphosate acid with the ammonia. Optionally one or more ports for venting water vapor and/or excess ammonia can be present between the ammonia injection port and the output end; however it is generally preferred that such venting occur only at the output end itself, through the discharge aperture for the ammonium glyphosate paste.

The type of apparatus just described, namely a continuous single- or twin-shaft mixer/kneader or solids processor, has been found particularly suitable when anhydrous ammonia is used, either in the gaseous or liquid state. When ammonia is injected at some distance from the input end, the atmosphere within the chamber in the vicinity of the ammonia injection port becomes rich in ammonia, and the large gas-paste interface ensures rapid and efficient reaction of the ammonia with the glyphosate acid. Rapid consumption of the ammonia in the reaction leads to a rather steep declining concentration gradient of ammonia in the internal atmosphere of the chamber, towards both the input and the output end.

When the ammonia injection port is located at a suitable distance from each of the input and output ends, when the apparatus is operated at a suitable shaft rotation speed, and when the glyphosate acid and anhydrous ammonia are fed continuously at close to a 1:1 mole ratio, the concentration of ammonia in the atmosphere at both ends of the chamber is normally so low that almost no ammonia is vented.

If the glyphosate acid is fed in the form of wet cake and no additional water, or only a small amount of additional water, is required, the degree of mixing needed before contact with the ammonia is minimal. In this situation, the ammonia injection port can if desired be located close to the input end of the chamber. Back-leakage of ammonia gas from the input end can be substantially prevented by arranging that screw elements on the shafts draw wet cake uninterruptedly into the chamber so that no air continuum is permitted to form between the outside and inside of the chamber at the input end.

Thus in an especially preferred process, (i) glyphosate acid in the form of wet cake is fed uninterruptedly by screw elements disposed in the aperture at the input end of the chamber in such a way that no air continuum forms that would permit back-leakage of ammonia at the input end, (ii) shaft rotation speed is such that residence time of glyphosate in the chamber is sufficient to permit completion of the reaction forming the ammonium glyphosate; and (iii) anhydrous ammonia is injected through a port located at a distance from the output end sufficient to result in substantially no venting of ammonia from the aperture at the output end.

Even where the apparatus is designed for operation with close to zero emission of ammonia, it will normally still be desirable to pass vented gases through a scrubber or equivalent device before release to the environment.

With the information presented herein, one of skill in the art will find it straightforward by routine testing to establish, for any particular apparatus of the type just described, a suitable shaft rotation speed (affecting glyphosate acid feed rate as well as residence time in the chamber), water feed rate and ammonia injection point (ammonia injection rate being tied to glyphosate acid feed rate) to operate the process of the present invention efficiently with minimal venting of ammonia. Where the apparatus has replaceable screw elements and pin and/or paddle elements on the shafts, the skilled person will also readily be able, by routine testing, to identify an optimum configuration of such elements.

Within the range of about 10% to about 25% specified, the amount of water present in the initial reaction mass is not critical, although, as indicated above, an optimum amount of water for a particular apparatus can be determined by one of skill in the art. As guidance, where 100 parts by weight of glyphosate acid are mixed with 10 parts by weight of ammonia (both expressed on a water-free basis) and no other ingredients except water are added in the reaction step, a suitable amount of water is about 12 to about 37 parts by weight. Part or all of this water can be present in the glyphosate acid or ammonia composition added. For example, if 10 parts by weight ammonia in the form of aqueous ammonia (29% by weight ammonia, 71% by weight water) are added to 100 parts by weight glyphosate acid in the form of wet cake having 10% moisture content, the total amount of water present in these ingredients is about 35.6 parts by weight and the maximum amount of additional water to be added is about 1.4 parts by weight. In general no addition of water is needed in such a situation. However, if 10 parts by weight anhydrous ammonia are added to 100 parts by weight glyphosate acid in the form of wet cake having 12% moisture content, the total amount of water present in these ingredients is only about 13.6 parts by weight, and up to about 23.4 parts by weight of additional water can be added.

The two principal considerations in selecting an optimum amount of water are: first, that the paste resulting from the mixing step is sufficiently wet to be readily homogenized with the degree of energy available in the mixing system used, so that the acid-base reaction proceeds smoothly and completely; and second, that sufficient water is present to contribute usefully to dissipation of heat by evaporative cooling. In some types of high-energy mixing or kneading equipment having an effective conductive cooling system in the form, for example, of a water jacket, a relatively stiff paste having relatively low moisture content is acceptable, whereas in lower-energy equipment or equipment having a less effective conductive cooling system it can be desirable to form a wetter, more fluid paste.

Any grade of particulate glyphosate acid can be used. Technical grade glyphosate acid, for example in the form of wet cake having about 8% to about 15% moisture content, has been found to be suitable, but if desired the glyphosate acid can be pre-dried and/or pre-ground.

If the glyphosate acid is supplied in the form of wet cake, it may be necessary to employ specially designed equipment as described hereinafter in order to maintain a constant feed rate. Glyphosate acid wet cake is a somewhat cohesive material that does not flow freely without the application of external force. Even when agitated, the wet cake tends to form "bridges" in static zones within the feed vessel where the wet cake is not in motion. Over time these bridges can grow to the point that no wet cake flows from the feed vessel; but well before this occurs the reduced feed rate of glyphosate results in the use of an excess of ammonia in the downstream reaction step. As explained elsewhere herein, this excess generally leads to the production of unsatisfactory ammonia glyphosate product. When mixing step (a) is carried out continuously, it is therefore important that the glyphosate acid wet cake be fed using equipment that reliably maintains a constant feed rate and that is not susceptible to bridging. A further complication is that the moisture content of the wet cake is not constant.

Figure 2:
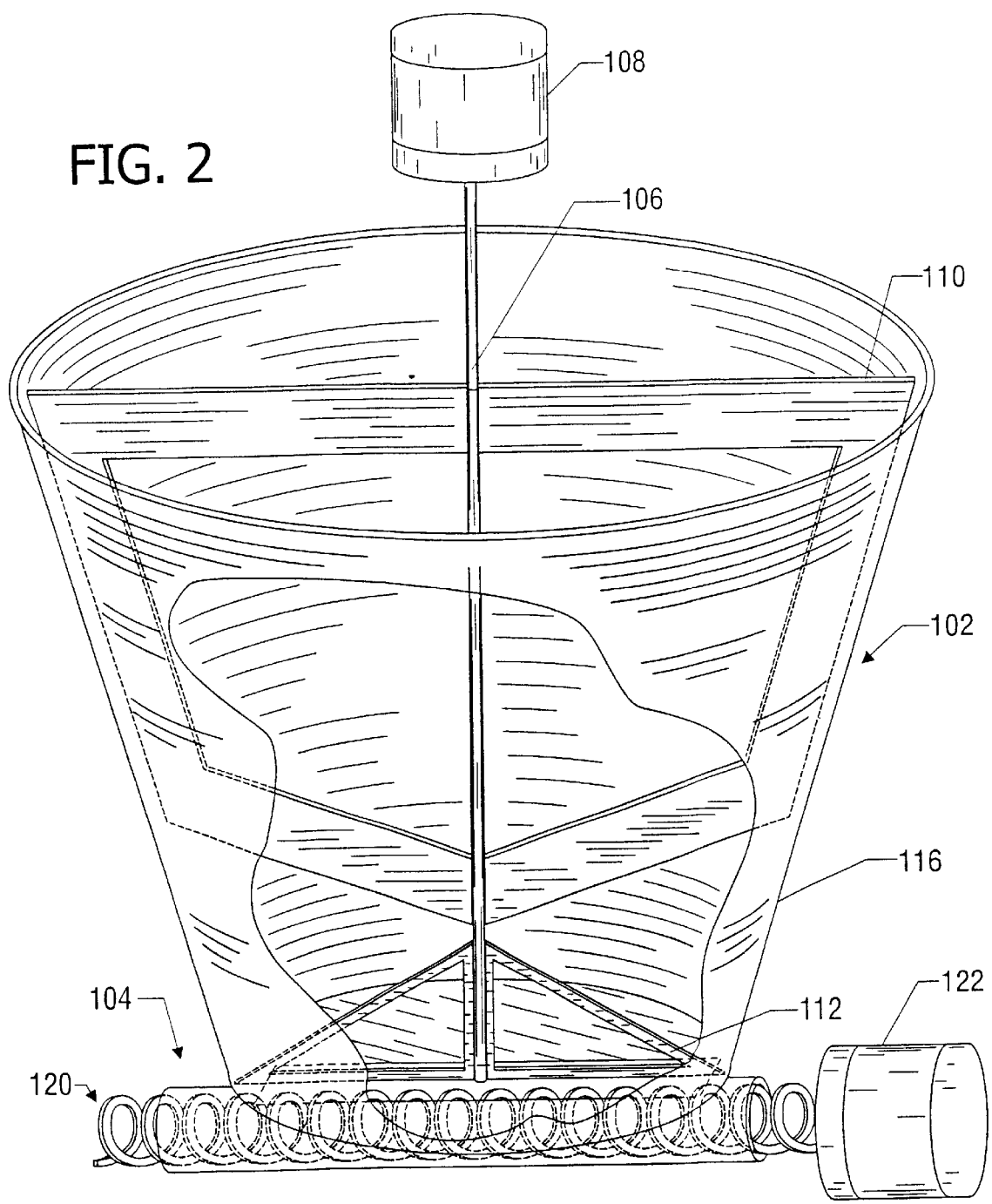
FIGS. 2 through 4 show a number of views of a gravimetric feeder suitable for supplying glyphosate acid wet cake at a constant feed rate in the process of the invention.

FIG. 2 depicts a suitable feeding apparatus that is designed to minimize the amount of bridging. The apparatus includes an upper feeder 102 and a lower feeder 104. The upper feeder includes a feed hopper 116 equipped with an agitator 106 driven by a motor 108. Other types of active upper feeder are known, such as hoppers of various shapes having thin walls that are made to flex inward to drive the feed material toward the bottom of the hopper. Such units are unsuitable for the feeding of glyphosate wet cake, however, because they do not impart sufficient motion to the interior of the feed material to break the bridges as they form.

The agitator includes upper blades 110 and lower blades 112. The upper blades are preferably open paddles shaped so as to fit closely within the walls of the hopper. Lower blades 112 are placed so as to maintain a minimum clearance, preferably less than about $\frac{1}{16}$", from the top of the screw in the lower feeder so as to prevent accumulation of wet cake on the bottom plate. Commercially available feeders that employ this agitator design typically provide about $\frac{1}{4}$" clearance between the blade edges and the bottom plate; the applicants have found that when the clearance is this large glyphosate wet cake can accumulate on the plate. As shown more clearly in FIGS. 3 and 4, bottom plate 114 is formed with an integral trough 118 that forms the housing of lower feeder 104. If the clearance is too great between the blades and the bottom plate, bridges of wet cake may form across the top of this trough, impeding or stopping the flow of wet cake to the lower feeder.

It is also important to maintain careful control of the agitation speed. If the agitator rotates too quickly, it may force material into the lower feed unit faster than the screw can transport the wet cake into the reaction apparatus. If the agitation speed is too low, the agitator will not break up the bridges forming in the hopper.

Figure 3:
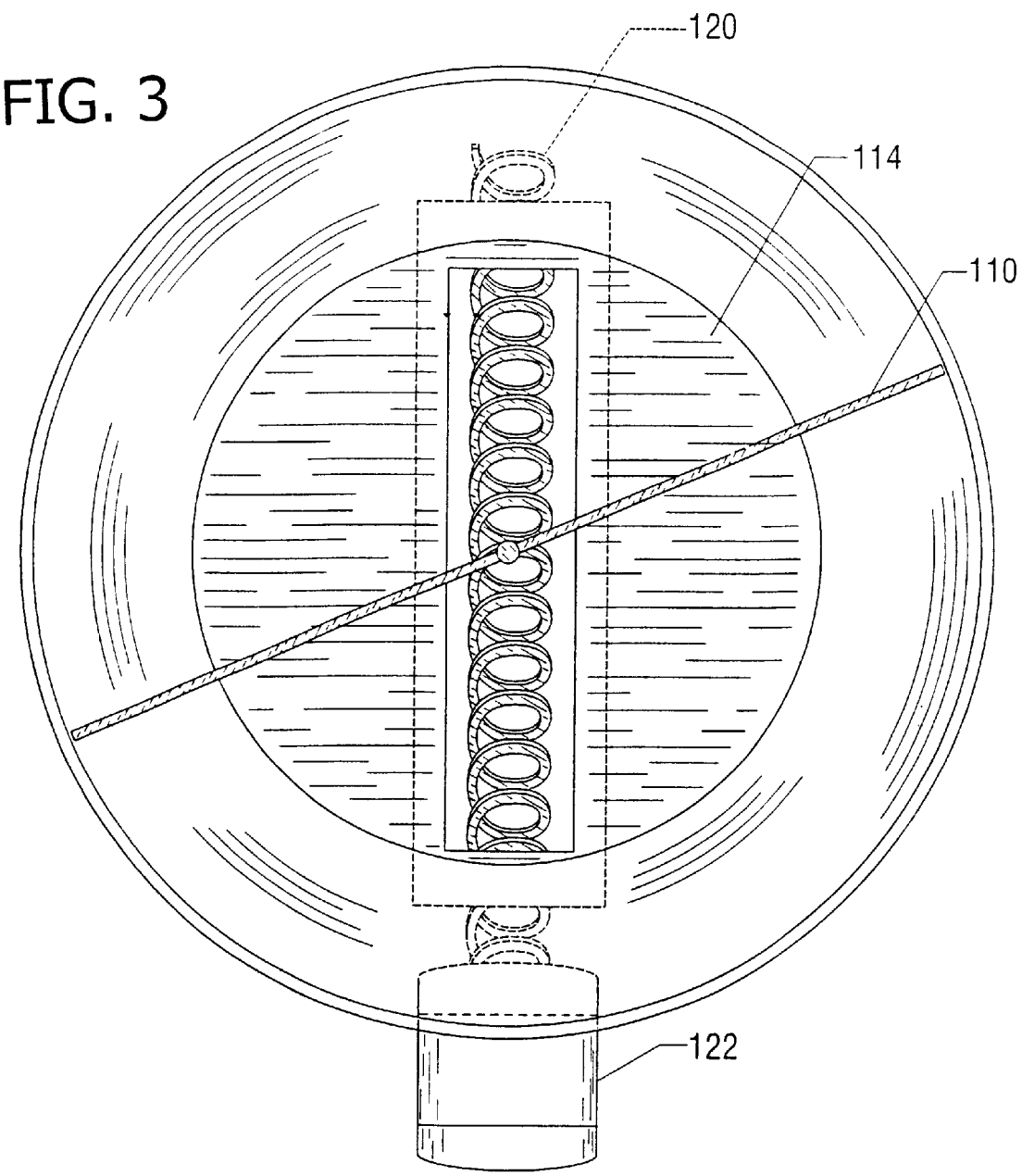
Figure 4:
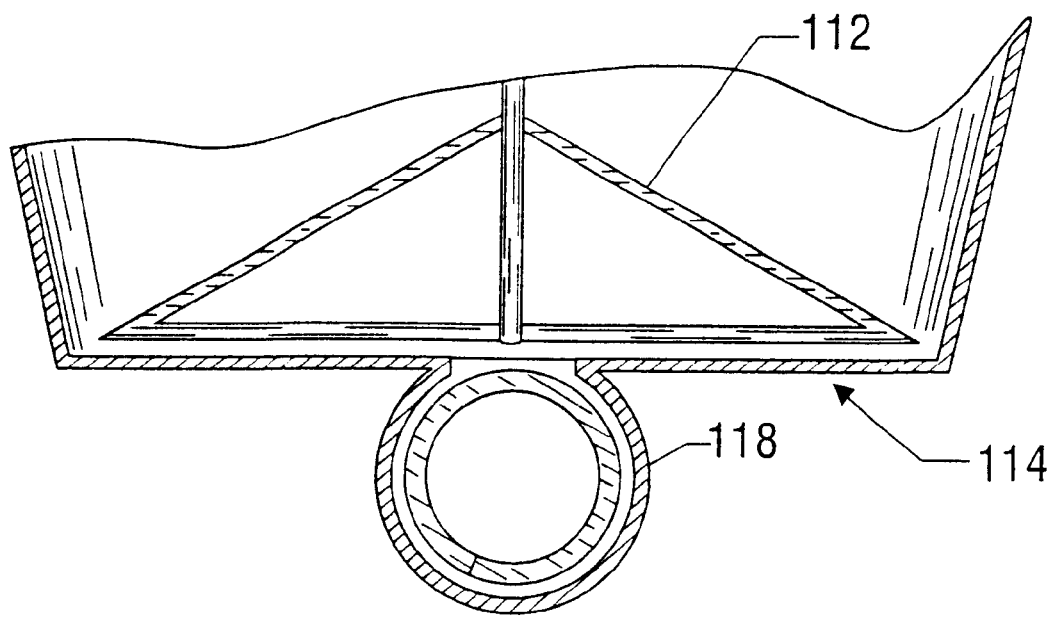

Lower feed unit 104 is preferably a screw feeder equipped with screw 120 and driven by motor 122. Although many varieties of screw may be suitable when the moisture content of the wet cake is relatively low, most types of screw do not function well when the wet cake contains sufficient moisture that bridging is possible. One screw configuration that does work well, even at higher moisture levels, is a single-helix, open-spiral auger without a center shaft. FIG. 3 depicts the preferred design of screw 120.

Preferably anhydrous or aqueous ammonia is added in an approximately stoichiometric amount to result in the formation of monoammonium glyphosate. If less than 1 mole of ammonia is added per mole of glyphosate acid, a fraction of the glyphosate acid will remain unneutralized. If this fraction is small, for example less than about 20%, resulting in the presence of at least about 4 moles of ammonium glyphosate per mole of unneutralized glyphosate acid, it is generally not unacceptable. However, it is preferred that about 0.95 to about 1.05 moles of ammonia are added per mole of glyphosate acid.

The reaction of ammonia with glyphosate acid is exothermic. Continued mixing of the paste and creation of a large gas-paste interface is important to provide efficient heat transfer as well as to ensure a complete and uniform reaction. The heat generated in the reaction results in evaporation of some of the water in the paste, this evaporation typically contributing usefully to avoidance of overheating. Normally in a substantially enclosed reaction chamber the temperature of the reaction mass and the resulting ammonium glyphosate paste is close to 100° C. Typically evaporation results in a decrease of about 2 to about 10 percentage points in the moisture content of the paste in the course of the reaction step, so that by the time the reaction step is complete the moisture content of the paste is typically about 5% to about 20% by weight. This moisture content should be measured after the paste has been allowed to cool to about 50° C. to about 70° C., as a substantial amount of water can be given off by evaporation during such cooling. To avoid the necessity for application of heat and/or vacuum to drive off further water, it is preferred that the amount of water present in the initial reaction mass is not greater than about 15% by weight, leading to a moisture content of the resulting ammonium glyphosate paste that is not greater than about 10%, more preferably not greater than about 7%, by weight.

Where ammonia is added in the form of aqueous ammonia (ammonium hydroxide), the heat of reaction with glyphosate acid is sometimes insufficient to drive off enough water to bring the moisture content of the resulting paste into the desired range of about 5% to about 15%, preferably about 5% to about 10%, more preferably about 5% to about 7%, by weight. In such a situation, heat can optionally be supplied via the jacket to increase water evaporation; additionally or alternatively, further reduction in moisture content of the paste can be effected by application of heat and/or vacuum to the paste after completion of the reaction step. Any moisture reduction or partial drying method known in the art can be used.

Clearly, to minimize costs of additional heating and to maximize throughput by elimination of unnecessary process steps or residence time, it is preferable to add no more water at the beginning of the process than is necessary to provide a suitable paste consistency and sufficient evaporative cooling, and to result in an ammonium glyphosate paste having about 5% to about 10%, more preferably about 5% to about 7%, moisture content, that is downstream processable without further reduction in moisture content. For this reason, anhydrous ammonia is preferred over aqueous ammonia, and the amount of water introduced, including moisture associated with the glyphosate acid, is preferably about 10% to about 15% by weight of all materials being mixed in the vessel.

Anhydrous ammonia can be added in the liquid or gaseous state. If gaseous ammonia is used, the heat that must be dissipated by evaporation of water and/or by means of a cold water jacket is greater than if liquid anhydrous ammonia is used.

The ammonium glyphosate paste produced by the process described in detail above can be packaged as a concentrate herbicidal composition, either as such or dried, for example by drum drying to form solid flakes. However, this paste has been found surprisingly to be suitable as an intermediate in preparation of a dry granular herbicidal composition as more particularly described below. What is especially surprising is that the ammonium glyphosate in the paste form generated herein has been found to have the required absorbency and/or adsorbency properties to enable efficient formulation as a dry granular herbicidal composition with surfactant at up to about 25% by weight of the finished composition, by a process of extrusion granulation. Previously, only solid-state reaction processes conducted in presence of very low amounts of water, for example about 7 parts or less by weight of water per 100 parts by weight of dry ingredients, have given an ammonium glyphosate product suitable for such further formulation. The process of the present invention therefore surprisingly combines rapidity, completeness and uniformity of reaction (not readily obtainable in a solid-state reaction system) with the desired ammonium glyphosate product quality for downstream processing.

The surfactant to be mixed with the ammonium glyphosate paste having about 5% to about 15%, preferably about 5% to about 10%, moisture content in step (b) is added in an amount of about 10 to about 25 parts by weight of total surfactant to an amount of about 90 to about 75 parts by weight respectively of ammonium glyphosate on a dry basis, giving a weight ratio of total surfactant to ammonium glyphosate of about 1:9 to about 1:3. The surfactant typically helps to condition the paste to form an extrudable wet mix; however, a major function of the surfactant is to enhance herbicidal efficacy of the finished product. The surfactant component can consist of a single type of surfactant, or it can comprise two or more surfactant materials. Where two or more surfactant materials are used, they can be added individually to the ammonium glyphosate paste or they can be first blended together and then added in mixture. Other materials, including water and/or glycols, can optionally be admixed with the surfactant or surfactants prior to addition to the ammonium glyphosate paste.

Any class of surfactant can be used; however, it is generally preferred that at least one surfactant added in step (b) is cationic or amphoteric. An exception is the class of surfactants known as alkyl polyglycosides (APGs), which are nonionic but which are also among preferred surfactants for use in the present invention. A further exception is polyoxyethylene $C_{16-22}$ alkylethers, also nonionic. Among illustrative classes of cationic and amphoteric surfactants useful in the invention are alkylamines, alylammonium salts, alkylamine oxides, alkylbetaines, alkyletheramines, alkyletherammonium salts and alkyletheramine oxides. Polyoxyethylene derivatives of such cationic and amphoteric surfactants are particularly preferred. The term "alkyl" is used in the present context to denote one or more linear or branched, saturated or unsaturated hydrocarbyl chains having, unless otherwise specified, about 8 to about 22 carbon atoms.

The surfactant or surfactant blend is preferably added in a liquid state; even in the case of a liquid surfactant it is generally helpful to heat the surfactant to bring it into a readily flowable condition before adding it to the ammonium glyphosate. Solid surfactants can be added in the solid state or alternatively can be heated to a temperature above their melting point and added in the liquid state.

An optimum weight ratio of total surfactant to ammonium glyphosate depends, among other things, on the type of surfactant or surfactants used. Such an optimum ratio will often be a compromise between, on the one hand, providing sufficient surfactant to give a high degree of herbicidal efficacy of the finished product, and on the other hand, limiting the amount of surfactant to avoid the finished granules being sticky or tending to aggregate to form lumps. Finding such an optimum weight ratio is a matter of routine testing by one of skill in the art. In general, the optimum weight ratio is about 1:6 to about 1:3, where the surfactant selected is a polyoxyethylene alkylamine, for example polyoxyethylene (20) tallowamine, a particularly useful weight ratio has been found to be about 1:4.

Addition of surfactant to ammonium glyphosate paste immediately on completion of the reaction step, without permitting the paste to cool, is generally unsatisfactory, the surfactant in such conditions failing to mix intimately with the paste. Some surfactants are more tolerant than others in this respect, and a suitable temperature for the paste at the time of surfactant addition can be determined by one of skill in the art by routine testing. However, for most surfactants it is preferred to add the surfactant to paste that has been cooled to about 25° C. to about 75° C., more preferably about 50° C. to about 70° C. A paste temperature of about 70° C. has been found especially satisfactory.

In one embodiment of the present invention, mixing of ammonium glyphosate paste and surfactant to form an extrudable wet mix is carried out in the same vessel or apparatus as the foregoing reaction step. According to the present invention the addition of surfactant occurs after the reaction of glyphosate and ammonia is substantially completed; addition of the surfactant prior to or during the reaction step has generally been found to be detrimental to the smooth operation of the process.

Preferably in such an embodiment, step (a) occurs in a continuous single- or twin-shaft mixer/kneader or solids processor as described above, step (b) occurs in the same apparatus, and the operation of steps (a) and (b) proceed continuously. Surfactant enters the chamber at a point downstream from the input end, so that an ammonium glyphosate paste has already been formed, and water vapor vented, by the time the surfactant is added. The rates of metering of glyphosate, ammonia and water near the input end and of surfactant downstream are controlled so that the ingredients are mixed in the desired proportions. The zone of the processor immediately upstream from the point of introduction of the surfactant can if necessary be cooled, for example by circulation of chilled water in a water jacket, to ensure the paste is an appropriate temperature for addition of the surfactant as described above.

In another embodiment, step (a) occurs in a continuous single- or twin-shaft mixer/kneader or solids processor as described above, and the resulting ammonium glyphosate paste is fed continuously to a separate apparatus, for example a continuous kneader, where step (b) is performed.

In step (b), mixing is continued until a homogeneous wet mix, preferably having a dough-like consistency, is obtained.

Other materials can optionally be added to the mix in step (a) and/or step (b). For example, a small amount of sodium sulfite can be added to inhibit nitrosamine formation. Other inorganic salts bringing useful benefits can also be added if desired. For example, ammonium sulfate, known to enhance herbicidal effectiveness of glyphosate compositions, can be included in the mix. In one embodiment, a second herbicidal active ingredient is added.

The second herbicidal active ingredient, if included, can be, like glyphosate, an acid which is converted to its ammonium salt during mixing with ammonia in step (a). Illustrative examples of such herbicides are acifluorfen, asulam, benzolin, bentazon, bilanafos, bromacil, bromoxynil, chlormben, clopyralid, 2,4-D, 2,4-DB, dalapon, dicamba, dichloroprop, diclofop, endothall, fenac, fenoxaprop, flamprop, fluazifop, flumiclorac, fluoroglycofen, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr. Alternatively, any of these herbicidal active ingredients can be added already neutralized and in the form of a salt.

Salts of the above herbicides are generally water-soluble and the end-product of the process is a water-soluble granular formulation. Optionally, a water-insoluble herbicidal active ingredient can be included in the mix, which case the end-product of the process is a water-disposable granular formulation. Water-insoluble herbicides useful in this embodiment of the invention illustratively include acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, clorthal-dimethyl, chlorothiamid, cinmethylin, cinosulfuron, clethodim, clodinafop-propargyl, clomazone, clomeprop, cloransulam-methyl, cyanazine, clycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxaxin, fluometuron, fluorochloridone, fluoroglycofen-ethyl, flupoxam, flurenol, fluridone, fluoroxypyr-1-methylheptyl, flurtamone, fluthiacet-methyl, fomesafen, halosulfuron, haloxyfop-methyl, hexazinone, imazosulfuron, indanofan, isoprofuron, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, melsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizlofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthlyazine, terbutyrn, thenylchlor, thiazopyr, thifensulfuron, thiobencarb, tiocarbazil, tralkoxydim, triallate, triazulfuron, tribenuron, trietazine, trifluralin, triflusulfuron and vernolate.

The next step, i.e., step (c), of the process of the present invention is a granulating step that comprises extruding the wet mix to form extrudate strands that break to form moist coherent granules. Extrusion is preferably carried out using a low-pressure radial or twin-dome extruder. The wet mix can be fed to the extruder by rotating screws which are also involved in the mixing of ingredients in steps (a) and (b); by this means or by analogous means the whole sequence of process steps (a) through (c), and, if desired, (d) and optionally (c), can be operated as a continuous process.

The wet mix is extruded through screens having apertures preferably of diameter about 0.5 to about 2 mm, more preferably about 0.6 to about 1.2 mm. The extrudate emerging from the screens initially forms elongated strands which tend to break spontaneously to form short cylindrical granules. If the strands do not break readily it may be necessary to add a cutting device at the extruder head; however, if the ammonium glyphosate powder has the desired absorption and/or adsorption properties and the amount of water added is within the optimum range as described above, a cutting operation is usually not necessary.

Immediately after extrusion, the granules are moist and coherent, but are not sticky and do not agglomerate. At this point the granules can, if desired, be subjected to a rolling or tumbling action, for example in a tumbler or spheronizer, to give them a more rounded shape and to make them more uniform in size.

The next step, i.e., step (d) of the process of the present invention, involves drying the granules. Any known drying method can be used, but a preferred method is fluid bed drying. Preferably a continuous fluid bed dryer is used, with continuous inward feed from the extruder and continuous outward feed, for example to a holding vessel or packaging unit, optionally via a classifying step as indicated below. The granules are preferably dried to a moisture content below about 1%, more preferably below about 0.5% by weight.

After drying, the granules can be packaged or held in a hopper or other storage vessel until ready for packaging, but it is generally preferred to first classify the granules, for example by sieving, to retain only those in a desired size range. This is optional step (c) of the process of the present invention. An illustrative size range to be retained is larger than 40 mesh (about 0.6 mm) and smaller than 5 mesh (about 5 mm). Over- and under-sized granules or fragments or aggregates thereof can be recycled by adding them to the wet mix prior to extrusion.

EXAMPLES

The following Examples are provided for illustrative purposes only and are not intended to limit the scope of the present invention. The Examples will permit better understanding of the invention and perception of its advantageous and certain variations of execution.

Example 1

This Example illustrates a process of the invention using liquid anhydrous ammonia, where the mixing step is operated as a continuous process. The mixing apparatus used for preparation of ammonium glyphosate paste was a jacket co-rotating twin-screw mixer with 2 inch (51 mm) diameter screws, manufactured by Readco of York, Pa. Chilled water was circulated through the jacket.

Glyphosate acid in the form of wet cake having 11% moisture content was metered into the input end of the mixer at a rate of 20.3 kg/h. Liquid anhydrous ammonia was injected into the mixer through a port near the input end at a rate of 2.0 kg/h. The only water in the mix was that contained in the glyphosate wet cake, providing an initial moisture content of 10% by weight. The heat of reaction of the glyphosate acid and ammonia caused evaporation of water, the resulting water vapor being exhausted at the output end of the mixer. At this point, the ammonium glyphosate paste had a moisture content of 7.6% by weight. A 1% aqueous solution of ammonium glyphosate prepared from the paste was found to have a pH of 3.5.

The ammonium glyphosate paste was fed from the mixture and 22 parts by weight of polyoxyethylene (20) tallowamine surfactant were added to 95 parts by weight of the ammonium glyphosate paste. After further mixing, the resulting paste was extruded through an extrusion die having 0.7 mm apertures to form moist coherent cylindrical granules which were then dried in a fluid bed dryer. The resulting dried granules had a moisture content of about 0.5% by weight and contained, on a water-free basis, 80% by weight ammonium glyphosate and 20% surfactant.

Example 2

This Example illustrates a process of the invention using gaseous anhydrous ammonia, where the mixing step is operated as a continuous process. The same mixing apparatus was used as in Example 1.

Glyphosate acid in the form of wet cake having 11% moisture content was metered into the input end of the mixer at a rate of 20.4 kg/h. Gaseous anhydrous ammonia was injected into the mixer through a port near the input end at a rate of 2.7 kg/h, and water was injected into the mixer at the input end at a rate of 1.8 kg/h. Together with the water contained in the glyphosate wet cake, this provided an initial moisture content of 16% by weight. The heat of reaction of the glyphosate acid and ammonia caused evaporation of water, the resulting water vapor being exhausted at the output end of the mixer. At this point, the ammonium glyphosate paste had a moisture content of about 13% by weight. A 1% aqueous solution of ammonium glyphosate prepared from this paste was found to have a pH of 4.1, indicating a degree of neutralization (ammonia/glyphosate mole ratio) very close to 1.

Example 3

This Example illustrates a process of the invention using gaseous anhydrous ammonia, where the mixing step is operated as a batch process. A jacketed planetary mixer was used for the mixing step.

Glyphosate acid in the form of wet cake having 11% moisture content was added to the planetary mixer in an amount of 400 g, together with 25 g water. Gaseous anhydrous ammonia in the amount of 50 g was added over a period of 3 minutes. The initial moisture content of the mix was 14.5% by weight. The heat of reaction of the glyphosate acid and ammonia caused evaporation of water, resulting in the ammonium glyphosate paste having a moisture content of about 10% by weight. A 1% aqueous solution of ammonium glyphosate prepared from this paste was found to have a pH of 4.0, indicating a degree of neutralization (ammonia/glyphosate mole ratio) very close to 1.

To the ammonium glyphosate paste in the planetary mixer was added 94 g of polyoxyethylene (20) tallowamine surfactant with further mixing. The resulting paste was extruded through an extrusion die having 0.7 mm apertures to form moist coherent cylindrical granules which were then dried in a fluid bed dryer. The resulting dried granules had a moisture content of about 0.5% by weight and contained, on a water-free basis, 80.7% by weight ammonium glyphosate and 19.3% surfactant.

Example 4

This Example illustrates a process of the invention using liquid anhydrous ammonia, were the mixing step is operated as a continuous process. The mixing apparatus used for preparation of ammonium glyphosate paste was a jacketed co-rotating twin-screw mixer with 5 inch (127 mm) diameter screws, manufactured by Readco of York, Pa. Chilled water was circulated through the jacket.

Glyphosate acid in the form of wet cake having 12.3% moisture content was metered into the input end of the mixer at a rate of 140.3 kg/h. Liquid anhydrous ammonia was injected into the mixer through a port near the input end at a a rate of 12.5 kg/h, and water was injected into the mixer at the input end at a rate of 2.7 kg/h. The heat of reaction of the glyphosate acid and ammonia caused evaporation of water, the resulting water vapor being exhausted at the output end of the mixer. At this point, the ammonium glyphosate paste had a moisture content of 5.5% by weight. A 1% aqueous solution of ammonium glyphosate prepared from this paste was found to have a pH of 4.0.

The ammonium glyphosate paste was fed from the mixer and 20 parts by weight of polyoxyethylene (20) tallowamine surfactant were added to 80 parts by weight of the ammonium glyphosate paste. After further mixing, the resulting paste was extruded through an extrusion of die having 1.0 mm apertures to form moist coherent cylindrical granules which were then dried in a fluid bed dryer. The resulting dried granules had a moisture content of about 0.5% by weight and contained, on a water-free basis, 79% by weight ammonium glyphosate and 21% surfactant.

Example 5

This Example illustrates a process of the invention using aqueous ammonia, where the steps of mixing and reacting glyphosate acid and ammonia to form an ammonium glyphosate paste, mixing the paste with surfactant to form an extrudable wet mix, and extruding the wet mix to form granules are operated as a continuous process in a single apparatus. The apparatus used was a DNDG-62 twin-screw compound/extruder with 62 mm co-rotating screws, manufacturing by Buhler AG of Uzwil, Switzerland. Each of the screws, in addition to having screw elements of various lengths and pitches, was fitted coaxially with shearing and kneading elements. The screws were housed in a series of modular jacketed chamber sections known as barrels.

For the present Example, the screws had a length/diameter ratio of 40 and were housed in a series of 9 barrels, numbered from the input end. Barrel 1 had an inlet for solid feed and barrels 2 and 8 had ports for liquid feed. Barrel 2 was chilled, barrels 3 and 4 were heated to 130° C., barrels 5–7 were heated to 150° C. and barrel 8 was heated to 120° C. Barrels 1 and 9 were neither chilled nor heated. A vacuum of −0.6 bar was applied to barrels 4 to 6 for removal of water vapor. Barrel 9 fed directly to an extruder head. The screws were operated at 135 rpm, to give a production rate of extrudate of about 128 kg/h.

Glyphosate wet cake having 13% moisture content was fed to barrel 1 at a rate of 100 kg/h. Aqueous ammonia (30% by weight) was fed to barrel 2 at 28.8 kg/h. No additional water was added. The initial moisture content of the reaction mask was about 25.7% by weight.

Liquid surfactant was fed to barrel 8 at 27.8 kg/h. The surfactant was a 4:1 by weight mixture of polyoxypropylene (8) ethoxytrimethylammonium chloride and polyoxyethylene (20) sorbitan lauryl ester. It is believed that reaction of the glyphosate acid with ammonia was substantially completed in barrel 2, with some reduction in moisture content of the resulting ammonium glyphosate paste. Thereafter, with application of heat to barrels 3–8 and vacuum to barrels 4–6, further reduction in moisture content of the paste occurred prior to extrusion. The moisture content of the extrudate was about 10%. The finished product, upon dissolution in water to make a 1% glyphosate a.e. by weight solution, had a pH of 4.1.

Example 6

This example illustrates the use of a gravimetric feeder to supply glyphosate acid wet cake at a constant feed rate according to the present invention. Glyphosate acid wet cake was fed using a Merrick Industries Model 570-EX gravimetric feeder, which included a 30 ft$^3$ hopper equipped with a motor-driven agitator as described hereinabove and a single-helix open spiral auger driven by a 2 horsepower motor. The feeder was tested at feed rates of 2716 lb/hr and 5432 lb/hr using two glyphosate acid wet cake samples, which had moisture contents of 12.2% and 15.7%. The feeder ran reliably even while additional wet cake was being added to the hopper. The results are shown in the following table.

| Target feed rate (lb/hr) | Normal wet cake 12.2% H$_2$O | | | High Moisture Wet Cake 15.7% H$_2$O | | |
|---|---|---|---|---|---|---|
| | Average feed rate | Standard deviation | Accuracy (%) | Average feed rate | Standard deviation | Accuracy (%) |
| 2716 | 2704 | 33 | −0.430 | 2695 | 26 | −0.773 |
| | 2768 | 92 | 1.922 | 2718 | 32 | 0.060 |
| 5432 | 5338 | 66 | −1.735 | 5410 | 74 | −0.396 |
| | 5427 | 146 | −0.097 | 5441 | 114 | 0.163 |

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A process for preparing a downstream processable ammonium glyphosate paste, comprising mixing in a suitable vessel (i) particulate glyphosate acid, (ii) ammonia in an amount of about 0.8 to about 1.25 moles per mole of the glyphosate acid, and (iii) water in an amount of about 10% to about 25% by weight of all materials being mixed in the vessel, thereby causing a reaction of the glyphosate acid and ammonia that generates heat causing partial evaporation of the water, and forms an ammonium glyphosate paste having a moisture content of about 5% to about 20% by weight.

2. The process of claim 1 wherein all or part of the water in the vessel is introduced as moisture associated with the glyphosate acid and/or as the water component of aqueous ammonia.

3. The process of claim 1 wherein (i) the ammonia is introduced as anhydrous ammonia; (ii) water is introduced, in whole or in part as moisture associated with the glyphosatic acid, in an amount of about 10% to about 15% by weight; and (iii) the ammonium glyphosate paste formed has a moisture content of about 5% to about 10% by weight and is downstream processable without further reduction in moisture content.

4. The process of claim 3 wherein the ammonia is introduced as liquid anhydrous ammonia.

5. The process of claim 3 that is a continuous process conducted in a mixing apparatus comprising:

(a) a substantially enclosed chamber elongated in a substantially horizontal dimension, having (i) at an input end an aperture suitable for introduction of the particulate glyphosate acid, (ii) at an output end an aperture suitable for discharge of the ammonium glyphosate paste, and (iii) between the input and output ends one or more ports suitable for introduction of ammonia and water; and having disposed therein (b) one or two rotatable shafts, each on an axis parallel to the elongated dimension of the chamber, each having one or more screw elements coaxial with the shaft and bearing a plurality of radially disposed pins and/or paddles, such that rotation of the shafts effects (i) feeding of the glyphosate acid into the chamber through the aperture at the input end, (ii) mixing of the glyphosate acid, ammonia and water to form a reaction mass having a large gas-paste interface, (iii) transport of the reaction mass and the resulting ammonium glyphosate paste towards the output end of the chamber, and (iv) discharge of the ammonium glyphosate paste from the aperture at the output end.

6. The process of claim 5 wherein (i) glyphosate acid in the form of wet cake is fed uninterruptedly by screw elements disposed in the aperture at the input end of the chamber in such a way that no air continuum forms that would permit back-leakage of ammonia at the input end; (ii) shaft rotation speed is such that residence time of glyphosate in the chamber is sufficient to permit completion of the reaction forming the ammonium glyphosate; and (iii) the ammonia is injected through a port located at a distance from the output end sufficient to result in substantially no venting of ammonia from the aperture at the output end.

7. A process according to claim 1, wherein said amount of ammonia is front about 0.95 to about 1.05 moles of ammonia per mole of glyphosate acid.

8. A process according to claim 1, wherein the moisture content of said ammonium glyphosate paste is from about 5% to about 10% by weight.

9. A process according to claim 8, wherein the moisture content of said ammonium glyphosate paste is from about 5% to about 7% by weight.

10. A process according to claim 1, further comprising mixing a second herbicidal active ingredient with said glyphosate acid, said ammonia and said water.

11. A process according to claim 10, wherein said second herbicidal active ingredient is present in acid or salt form is selected from the group consisting of acifluorefen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr.

12. A process according to claim 11, wherein said second herbicidal active ingredient is added to acid form and wherein said amount of ammonia comprises an additional amount sufficient to neutralize said second herbicidal active ingredient.

13. A process according to claim 11, wherein said second herbicidal active ingredient is added in the form of a salt.

14. A process according to claim 10, wherein said second herbicidal active ingredient is a water-insoluble herbicide.

15. A process according to claim 14, wherein said water-insoluble herbicide is selected from the group consisting of acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, clornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfuralin, ethanetsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluidone, fluroxypyr-1-methylheptyl, flurtamone, fluthiacet-methyl, fomesafen, halosulfuron, haloxyfop-methyl, hexazinone, imazosulfuron, indanofan, isoproturon, isouron, osoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sufometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate.

16. A process for preparing a dry granular herbicidal composition, comprising
(a) mixing in a suitable vessel (i) particulate glyphosate acid, (ii) ammonia in an amount of about 0.8 to about 1.25 moles per mole of the glyphosate acid, and (iii) water in an amount of about 10% to about 25% by weight of all materials being mixed in the vessel, thereby causing a reaction of the glyphosate acid and ammonia that generates heat causing partial evaporation of the water, and forms an ammonium glyphosate paste having a moisture content of about 5% to about 20% by weight, and thereafter, if the paste has a moisture content greater than about 15% by weight, applying heat and/or vacuum to reduce the moisture content of the paste to about 5% to about 15% by weight;
(b) thereafter adding to the paste, with mixing, one or more surfactants in a weight ratio of total surfactant to ammonium glyphosate of about 1:9 to about 1:3 to form an extrudable wet mix;
(c) extruding the wet mix to form extrudate strands that break to form moist coherent granules; and
(d) drying the granules to produce the dry granular composition.

17. The process of claim 16 that comprises a further step (e) of classifying the dried granules to remove or recycle granules, fragments of granules and aggregates of granules that are outside a desired size range.

18. The process of claim 16 wherein, in the mixing step (a), all or part of the water in the vessel is introduced as moisture associated with the glyphosate acid and/or as the water component of aqueous ammonia.

19. The process of claim 16 wherein, in the mixing step (a), if the ammonium glyphosate paste on completion of the reaction has a moisture content greater than about 10% by weight, heat and/or vacuum is applied to reduce the moisture content of the paste to about 5% to about 10% by weight.

20. The process of claim 16 wherein, in the mixing step (a), (i) the ammonia is introduced as anhydrous ammonia; (ii) water is introduced, in whole or in part as moisture associated with the glyphosate acid, in an amount of about 10% to about 15% by weight; (iii) the ammonium glyphosate paste formed has a moisture content of about 5% to about 10% by weight; and (iv) no heat or vacuum is applied to further reduce the moisture content of the paste prior to step (b).

21. The process of claim 20 wherein the ammonia is introduced as liquid anhydrous ammonia.

22. The process of claim 20 that is a continuous process conducted in a mixing apparatus comprising:
(a) a substantially enclosed chamber elongated in a substantially horizontal dimension, having (i) at an input end an aperture suitable for introduction of the particulate glyphosate acid, (ii) at an output end an aperture suitable for discharge of the ammonium glyphosate paste, and (iii) between the input and output ends one or more ports suitable for introduction of ammonia and water; and having disposed therein
(b) one or two rotatable shafts, each on an axis parallel to the elongated dimension of the chamber, each having one or more screw elements coaxial with the shaft and bearing a plurality of radially disposed pins and/or paddles, such that rotation of the shafts effects (i) feeding of the glyphosate acid into the chamber through the aperture at the input end, (ii) mixing of the glyphosate acid, ammonia and water to form a reaction mass having a large gas-paste interface, (iii) transport of the reaction mass and the resulting ammonium glyphosate paste towards the output end of the chamber, and (iv) discharge of the ammonium glyphosate paste from the aperture at the output end.

23. The process of claim 22 wherein (i) glyphosate acid in the form of the wet cake is fed uninterruptedly by screw elements disposed in the aperture at the input end of the chamber in such a way that no air continuum forms that would permit back-leakage of ammonia at the input end; (ii) shaft rotation speed is such that residence time of glyphosate in the chamber is sufficient to permit completion of the reaction forming the ammonium glyphosate; and (iii) the ammonia is injected through a port located at a distance from the output end sufficient to result in substantially no venting of ammonia from the aperture at the output end.

24. The process of claim 11 wherein the extrudable wet mix formed in step (b) is of a consistency such that the extrudate strands formed in step (c) break spontaneously upon extrusion to form the granules.

25. The process of claim 11 wherein step (c) further comprises breaking or cutting the extrudate strands to form the granules.

26. The process of claim 11 wherein step (c) further comprises rolling and/or tumbling the moist granules to impart to the granules a more spherical shape and greater uniformity of size.

27. The process of claim 16 wherein the mixing step (a) is operated in a continuous mode.

28. The process of claim 16 wherein the mixing step (a) is operated in a batch mode.

29. The process of claim 16 wherein the entire process is operated in a continuous mode.

30. A process according to claim 16, further comprising the step of admixing with said one or more surfactants a material selected from the group consisting of water, glycols, and mixtures thereof before adding said one or more surfactants to the paste.

31. A process according to claim 16, wherein said one of more surfactants comprises at least one cationic surfactant or at least one amphoteric surfactant.

32. A process according to claim 31, wherein said cationic surfactant or amphoteric surfactant is selected from the group consisting of alkylamines, alkylammonium salts, alkylamine oxides, alkylbetaines, alkyletheramines, alkyletherammonium salts, alkyletheramine oxides; polyoxyethylene and polyoxypropylene derivatives thereof; and mixtures thereof.

33. A process according to claim 16, wherein said one or more surfactants comprises all least one alkyl polyglycoside surfactant.

34. A process according to claim 11, wherein said one or more surfactants comprises at least one polyoxyethylene $C_{16-22}$ alkylether surfactant.

35. A process according to claim 16, wherein said weight ratio of total surfactant to ammonium glyphosate is from about 1:6 to about 1:3.

36. A process according to claim 16, further comprising the step of cooling said paste before adding said one or more surfactants.

37. A process according to claim 36, wherein said paste is cooled to a temperature of about 25° C. to about 75° C. in said cooling step.

38. A process according to claim 36, wherein paste is cooled to a temperature of about 50° C. to about 70° C. in said cooling step.

39. A process according to claim 38, wherein said temperature is about 70° C.

40. A process according to claim 16, wherein step (b) further comprises adding a second herbicidal active ingredient to said paste.

41. A process according to claim 40, wherein said second herbicidal active ingredient comprises a water-soluble herbicide.

42. A process according to claim 41, wherein said water-soluble herbicide is selected from the group consisting of acifluorfen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr, salts thereof and mixtures thereof.

43. A process according to claim 40, wherein said second herbicidal active ingredient comprises a water-insoluble herbicide.

44. A process according to claim 43, wherein said water-insoluble herbicide is selected from the group consisting of acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlomitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, dielofop-methyl, diflufenican, dimefuron, dimepiperate, dimethachlor, dimethametryn, dimethenamid, dinitramine, dinoterb, diphenamid, dithlopyr, diuron, EPTC, esprocarb, ethalfuralin, ethamelsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofenethyl, flupoxam, flurenol, fluridone, fluroxypyr-1-methylheptyl, flurtamone, fluthiacet-methyl, fomesafen, halosulfuron, haloxylopmethyl, hexazinone, imazosulfuron, indanofan, isoproturon, isouron, osoxaben, isoxaflutole, isoxapyrifop, lactofen, lenacil, linuron, mefenacct, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norfluorazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyazmide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencab, tiocarbazil, tralkoxydim, triallate, triasulfuron, tribenuron, trietazine, trifluralin, triflusulfuron and vernolate.

* * * * *

UNITED STATES PATENT AND TRADEMARK OFFICE
CERTIFICATE OF CORRECTION

PATENT NO. : 6,605,568 B1
DATED : August 12, 2003
INVENTOR(S) : Massmann et al.

It is certified that error appears in the above-identified patent and that said Letters Patent is hereby corrected as shown below:

Column 5,
Line 34, "(c)" should read -- (e) --

Column 14,
Lines 7 and 39, "(c)" should read -- (e) --

Column 15,
Line 8, "mixture" should read -- mixer --
Line 37, "pII" should read -- pH --

Column 20,
Line 22, "(c)" should read -- (e) --

Signed and Sealed this

Twenty-eighth Day of June, 2005

JON W. DUDAS
*Director of the United States Patent and Trademark Office*